United States Patent
Evans

[11] 3,976,054
[45] Aug. 24, 1976

[54] NASOPHARYNGEAL SPECULUM

[76] Inventor: Howard F. Evans, 3955 Rice Road, Riverside, Calif. 92506

[22] Filed: Jan. 20, 1975

[21] Appl. No.: 542,345

[52] U.S. Cl. .................................. 128/4; 128/276
[51] Int. Cl.² ........................................ A61B 1/26
[58] Field of Search .................. 128/3, 9, 10–13, 128/136, 76 R, 276, 4; 32/33, 40

[56] References Cited
UNITED STATES PATENTS

| 1,128,317 | 2/1915 | Jaros | 128/12 |
| 2,896,611 | 7/1959 | Moore | 128/3 |
| 3,132,645 | 5/1964 | Gasper | 128/3 |

FOREIGN PATENTS OR APPLICATIONS

| 212,474 | 10/1908 | Germany | 128/11 |
| 361,581 | 11/1931 | United Kingdom | 128/3 |

Primary Examiner—Robert W. Michell
Assistant Examiner—Henry S. Layton
Attorney, Agent, or Firm—Eric T. S. Chung

[57] ABSTRACT

An improved nasopharyngeal speculum is disclosed. The subject speculum is especially designed to permit exposure of and provide a direct line of sight to the nasopharynx and thereby serve to facilitate the performance of medical procedures such as adenoidectomies and subsequent hemostasis.

11 Claims, 5 Drawing Figures

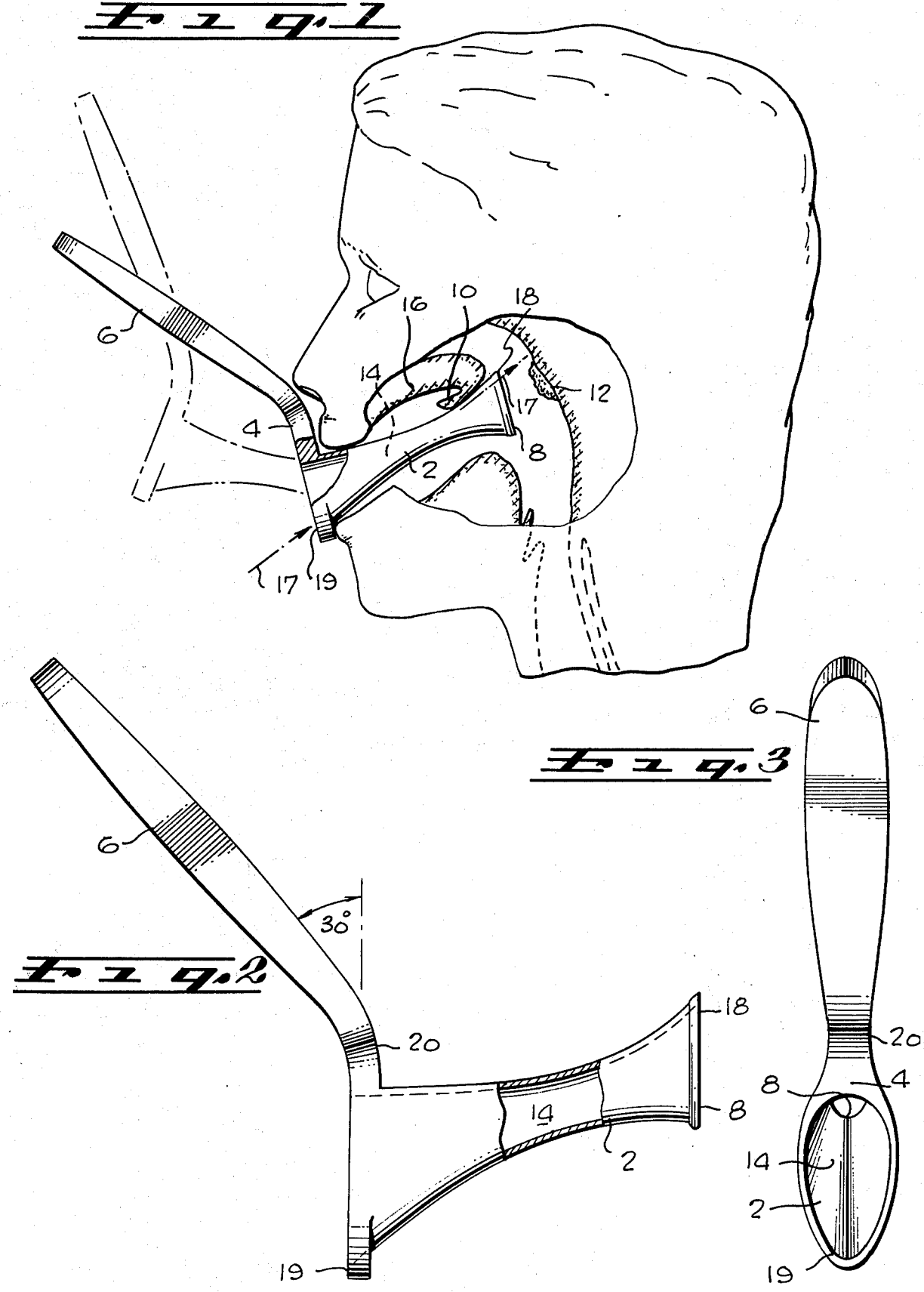

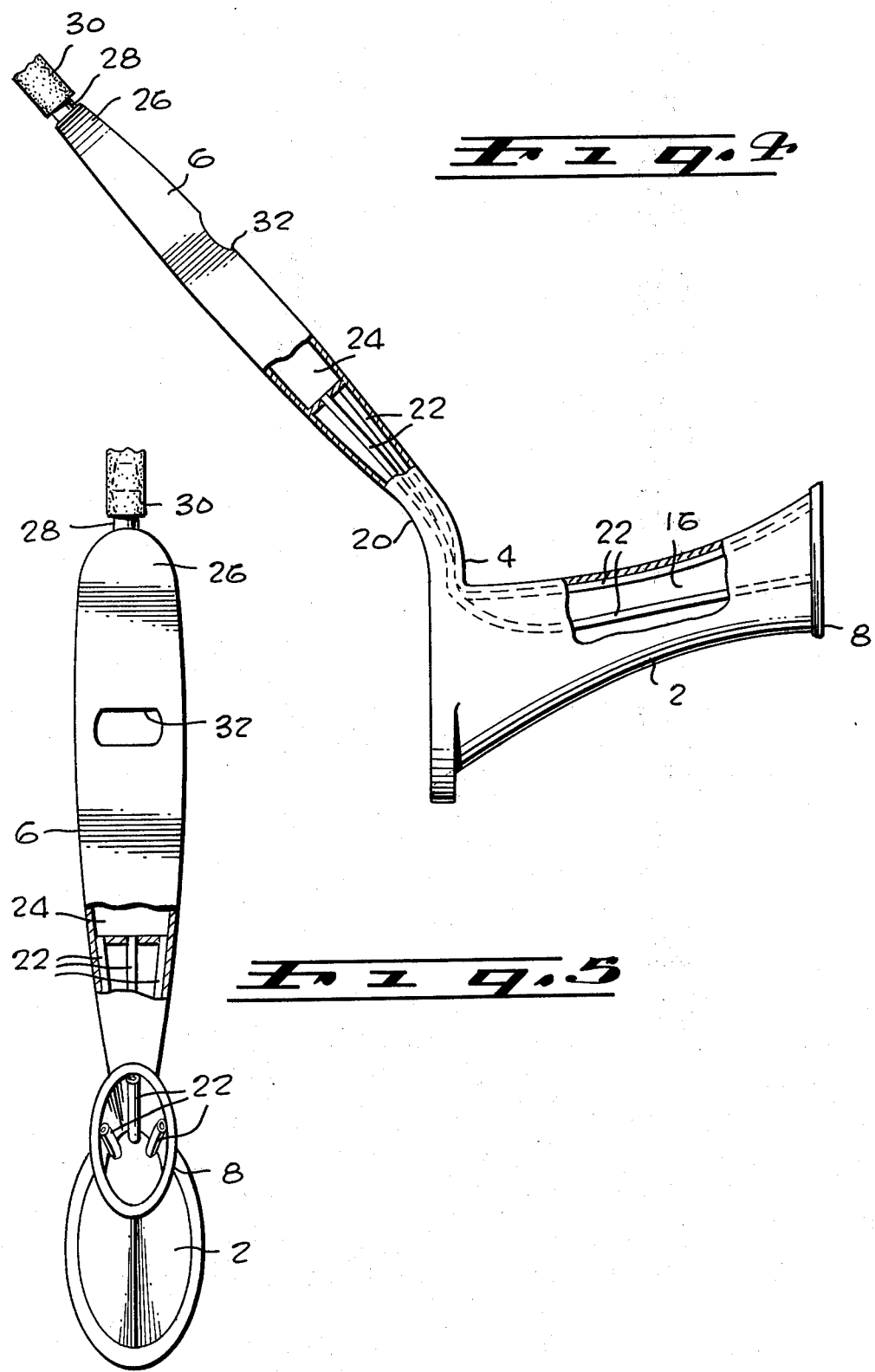

NASOPHARYNGEAL SPECULUM

BACKGROUND OF THE INVENTION

1. Field of the Invention

This invention generally relates to medical instruments useful in performing medical procedures in the area of the nasopharynx. More specifically, the present invention concerns an improved speculum that permits safe and effective exposure of the nasopharynx.

2. Description of the Prior Art

Adenoidectomy is a medical procedure that is commonly required to be performed on persons between the ages of 3 to 13. An estimated one percent (1%) of all adenoidectomies may be performed on older persons between the ages of 13 to 20.

Typically, such medical procedure simply involves removal of the adenoids by curettage. A degree of difficulty has in the past been experienced by the lack of a direct view of the nasopharynx, adenoids being essentially removed in the blind. Mirrors have been used to provide a limited degree of indirect viewing of the nasopharynx.

Hemostasis subsequent to adenoidectomies is, of course, required. Efficient hemostasis is naturally preferred to curtail the amount of blood lost. Although hemostasis ordinarily presents no extreme problem, as much as 200 cc's of blood may be lost using conventional procedures. Additional loss of blood is sufficiently possible and critical to prompt physicians performing adenoidectomies to have blood or plasma on hand should a transfusion be required. Clearly, such loss of blood is particularly critical for youngsters that are 3 to 5 years old and who have a limited supply of blood as compared to adults. While the amount of blood lost is less critical with adult patients, homostasis is oftentimes problematic due to the larger area of the nasopharynx involved and is certainly not simplified by the lack of a direct line of sight to the nasopharynx.

Conventionally, hemostasis is accomplished by the application of dry sponge pressure or the like. In more difficult cases, a nasopharyngeal pack which may be treated with a suitable conventional chemical is emplaced over the nasopharynx to stop bleeding. Typically, such a pack is positioned by having a string which is attached thereto threaded through the nasal cavity and pulled outward through the nostrils to have the pack drawn through a patient's mouth backwards around the soft palate to become lodged against the nasopharynx. Common practice is to leave such a pack in place for approximately 24 hours.

Modern methods of electro-coagulation have generally been unable to be used for hemostasis following adenoidectomies due to the lack of a direct line of sight to the nasopharynx.

It is accordingly the intention of the present invention to provide a medical instrument in the form of a nasopharyngeal speculum that permits a physician to expose and thereby have a direct line of sight to the nasopharynx such that medical procedures including electro-coagulation can be readily accomplished in conjunction with adenoidectomies and subsequent hemostasis.

SUMMARY OF THE INVENTION

Briefly described, the present invention involves a nasopharyngeal speculum for permitting exposure of and providing a direct line of sight to the nasopharynx. More particularly, the subject nasopharyngeal speculum is formed to have a tubular portion and a handle that is elbowed. The tubular portion is configured to have the open ends thereof flared to permit maximization of the area that is exposed and made accessible through the lumen of said tubular portion. Such curvature also serves to move the soft palate towards the hard palate and away from the throat when the leading end of the tubular portion is inserted into the mouth and urged against the soft palate.

BRIEF DESCRIPTION OF THE DRAWINGS

FIG. 1 is a schematic diagram illustrating the manner in which a speculum in accordance with the present invention is inserted into the mouth of a patient to expose the nasopharynx.

FIG. 2 is a schematic diagram illustrating a side, partially-fragmented view of a speculum in accordance with the present invention.

FIG. 3 is a schematic diagram illustrating a frontal view of the speculum shown by FIG. 2.

FIG. 4 is a schematic diagram illustrating a side, partially-fragmented view of an alternate embodiment of a speculum in accordance with the present invention.

FIG. 5 is a schematic diagram illustrating a rear view of the speculum shown by FIG. 4.

DETAILED DESCRIPTION OF THE PREFERRED EMBODIMENT

Referring to FIGS. 1, 2 and 3 of the drawings, a nasopharyngeal speculum in accordance with the present invention is shown to essentially include a tubular portion 2 which may be integrally formed at or attached to an end 4 of a handle portion 6. Use of the nasopharyngeal speculum simply involves insertion of a leading end 8 of the tubular portion 2 into the mouth of a patient followed by rotation of the handle 6 away from the face of the patient to have the leading end 8 pressed against the back of the soft palate 10 of a patient to provide a direct line of sight to the nasopharynx 12 through the lumen 14 of the speculum. As shown by FIG. 1, the soft palate 10 is thereby moved towards the hard palate 16 and away from a patient's throat by such manipulation of the speculum.

The respective ends of the tubular portion 2 may be moderately flared, as shown, to maximize the area at the nasopharynx that can be viewed and/or is accessable through the lumen 14. As is also evident from FIG. 2, such flaring need not be symmetrical; but rather may be shaped to minimize the divergency of the line of sight, along a broken line 17 extending between points 18 and 19 at opposite ends of the tubular portion 2, from the longitudinal axis of the tubular portion 2. Such shaping is intended to permit direct viewing of the deeper reaches of the nasopharynx.

Medical procedures dealing with the nasopharynx 12 may thereby be accomplished through the lumen 14 with the nasopharynx 12 in direct view. Such medical procedures may include biopsies of nasopharyngeal tumors and/or removal of certain tumors of the nasopharynx. Additionally, electro-coagulation procedures may be used to accomplish hemostasis in the region of the nasopharynx 12.

It has been found that using such electro-coagulation procedures as permitted by the subject invention, loss of blood is able to be reduced to 15–20 cc's following an adenoidectomy.

The handle 6 of the speculum is formed to have an elbow 20 near its junction with the tubular portion 2. As shown, the handle is formed to curve away from the leading end 8. It has been found that an angle of approximately 30° is highly suitable for the purpose of the subject invention, although other angles may be suitable for the subject purpose. Such elbow configuration for the handle 6 is required to permit the tubular portion 2 to be inserted into a patient's mouth at an angle permitting the leading end 8 to be comfortably passed beneath and beyond the soft palate 10 prior to having the handle 6 rotated or moved away from the patient's face to thereby depress the outer surface of the tubular portion 2 against the soft palate 10, as earlier described, to align the lumen 14 with the portion of the nasopharynx 12 to be viewed and/or operated on. Without such elbow configuration, the end of the handle 6 and/or the fingers of the physician gripping such handle 6 would strike a patient's face as the speculum is inserted into the patient's mouth and limit the degree to which the tubular portion 2 can be dipped away from the soft palate 10 before being moved thereagainst.

It is preferred that the nasopharyngeal speculum in accordance with the present invention be manufactured using electrically non-conductive material such that electro-coagulation procedures can be accomplished through the lumen 16 of the tubular portion 2. Such use of electrically non-conductive material is essential to the well being of the patient and facilitates the use of such electro-coagulation procedures by not requiring a physician to maintain the probe of an electro-coagulation device out of contact with the speculum. As is well known, such precaution is required to prevent and avoid inadvertant burning of the patient by the speculum itself when contacting the probe of the electro-coagulation device. Use of a non-conductive speculum also eliminates the possibility of electrical arcing between the speculum and probe and any undesirable dissipation of the electrical energy required for electro-coagulation.

The dimensions of a speculum should generally conform to the parameters of the human mouth. FIG. 2 generally illustrates an appropriate size for a speculum. However, a somewhat smaller size can be used to accommodate youngsters as may be desired and/or is necessary.

Referring now to FIGS. 4 and 5, an alternate embodiment of the subject invention includes the provision of tubing 22 extending from the leading end 8 of the tubular portion 2 through the lumen 16, along the interior surface thereof and upward into the handle 6 of the speculum which may be hollowed to communicate with a cavity 24 formed therein for its remaining length. The handle 6 would then itself perform the function of a tubing. The distal end 26 of the handle 6 is provided with a tubular connector 28 which may be readily attached to the end of a tubing 30 connected to a conventional suction unit. It is to be understood that the extent to which the tubing 22 extends into the handle can be varied as will be the length of the cavity 24 to a corresponding degree.

The speculum, when in use, will accordingly further serve to enable removal, by suction, of fluids or the like in the region of the nasopharynx as is often required in the course of medical procedures.

Manual control of the suction may be readily accomplished by having an aperture 32 provided in the handle 6 to create an exit for the cavity 24. The aperture 32 may then be covered, such as with a finger of a user, to have suction occur at the leading end 8 via the tubes 22. When uncovered, the aperture 30 would permit leakage of the vacuum provided by the suction unit and thereby prevent or frustrate suction through the tubing 22 even though the suction unit may continue operating.

From the foregoing discussion, it is now clear that the subject invention provides a nasopharyngeal speculum that allows exposure of, and provides a direct line of sight to, the nasopharynx to thereby enable the performance of medical procedures in the region thereof. It is further apparent that the subject invention may be used to further serve to allow removal, by suction, of fluids and the like from the region of the nasopharynx without the requirement for inserting additional medical instruments into the limited space provided in the mouth of a patient.

While a preferred embodiment of the present invention has been described hereinabove, it is intended that all matter contained in the above description and shown in the accompanying drawings be interpreted as illustrative and not in a limiting sense and that all modifications which fall within the scope and spirit of the invention may be made.

What is claimed is:

1. A nasopharyngeal speculum for providing a direct line of signt to the nasopharynx of humans, said nasopharyngeal speculum including:

a tubular portion having a pair of ends serving as a leading end and a viewing end, said tubular portion forming a lumen, said pair of ends being flared;

a handle portion having a bend proximate to a first end thereof forming a major handle section and a minor handle section on opposite sides of said bend, said viewing end of said tubular portion being attached to said first end of said handle portion with said major handle section being bent away from said leading end of said tubular portion; and conduit means for conducting a vacuum to said leading end of said tubular portion to allow suction thereat.

2. The nasopharyngeal speculum defined by claim 1, said tubular portion being electrically non-conductive.

3. The nasopharyngeal speculum defined by claim 1, said tubular portion having oblong openings at said leading and viewing ends thereof.

4. The nasopharyngeal speculum defined by claim 1, said speculum being electrically non-conductive.

5. The nasopharyngeal speculum defined by claim 1, said conduit means including:

an interior cavity extending for the length of said handle portion; and hose means mounted within said lumen and communicating with said interior cavity for conducting a vacuum in said interior cavity to said leading end of said tubular portion.

6. The nasopharyngeal speculum defined by claim 5, said handle portion having first and second apertures both communicating with said interior cavity, said first aperture being adapted to have a vacuum applied thereto from an independent suction unit, said second aperture permitting leakage of said vacuum therethrough when uncovered and preventing said leakage to permit conduction of said vacuum to said leading end when covered.

7. The nasopharyngeal speculum defined by claim 6, said tubular portion being electrically non-conductive.

8. The nasopharyngeal speculum defined by claim 7, said tubular portion having oblong openings at said leading and viewing ends thereof.

9. A nasopharyngeal speculum for providing a direct line of sight to the nasopharynx of humans, said nasopharyngeal speculum including:
   a tubular portion for forming a lumen and having a pair of ends serving as a leading end and a viewing end, said leading and viewing ends of said tubular portion being outwardly flared to form a tapered central portion intermediate said ends; and
   a handle portion having first and second ends, said first end being attached to said viewing end of said tubular portion, said handle portion having a bend therein intermediate said first and second ends to form a minor section near said first end and a major section near said second end, said major section of said handle portion being bent away from said leading end of said tubular portion whereby said major section of said handle portion is adapted to be grasped and held in front of a patient's face to facilitate viewing of said patient's nasopharynx.

10. The nasopharyngeal speculum defined by claim 9, said tubular portion being electrically non-conductive.

11. The nasopharyngeal speculum defined by claim 9, said tubular portion having oblong openings at said leading and viewing ends thereof.

* * * * *